(12) United States Patent
Speitling

(10) Patent No.: US 9,011,668 B2
(45) Date of Patent: Apr. 21, 2015

(54) ANTIMICROBIAL PROVISION OF TITANIUM AND TITANIUM ALLOYS WITH SILVER

(75) Inventor: Andreas Speitling, Heikendorf (DE)

(73) Assignee: Stryker Trauma GmbH (DE)

( * ) Notice: Subject to any disclaimer, the term of this patent is extended or adjusted under 35 U.S.C. 154(b) by 439 days.

(21) Appl. No.: 12/866,063

(22) PCT Filed: Dec. 2, 2008

(86) PCT No.: PCT/EP2008/066604
§ 371 (c)(1),
(2), (4) Date: Aug. 4, 2010

(87) PCT Pub. No.: WO2009/100792
PCT Pub. Date: Aug. 20, 2009

(65) Prior Publication Data
US 2010/0326835 A1    Dec. 30, 2010

(30) Foreign Application Priority Data
Feb. 11, 2008   (DE) .......................... 10 2008 008 517

(51) Int. Cl.
*C23C 14/16* (2006.01)
*C23C 14/48* (2006.01)
*C23C 14/58* (2006.01)
*C25D 11/26* (2006.01)
(Continued)

(52) U.S. Cl.
CPC ................. *C25D 11/26* (2013.01); *A61L 27/06* (2013.01); *A61L 27/306* (2013.01); *A61L 27/54* (2013.01); *A61L 2300/104* (2013.01); *A61L 2300/404* (2013.01); *C23C 14/16* (2013.01); *C23C 14/48* (2013.01)

(58) Field of Classification Search
CPC ........ C23C 14/16; C23C 14/48; C23C 14/58; C23C 14/5893; C23C 28/21; C25D 11/26
USPC ......... 205/105, 109, 121, 171, 174, 175, 188, 205/210, 322, 324; 148/239; 427/528
See application file for complete search history.

(56) References Cited

U.S. PATENT DOCUMENTS 6,267,782 B1 * 7/2001 Ogle et al. .................... 623/1.1
2002/0099449 A1 * 7/2002 Speitling .................. 623/23.72
(Continued)

FOREIGN PATENT DOCUMENTS

DE         4328999 A1      3/1995
EP         1207220 A1      5/2002
(Continued)

OTHER PUBLICATIONS

T. H. Teh et al: "Initial stages of plasma electrolytic oxidation of titanium", Corrosion Science, vol. 45, No. 12, Dec. 2003, pp. 2757-2768.
Ewald et al.: "Antimicrobial titanium/silver PVD coatings on titanium", Biomedical Engineering Online, Biomed Central LTD, London, GB, vol. 5, No. 1, Mar. 24, 2006, p. 22.
Wan et al.: "Surface modification of metal by ions implantation of silver and copper", Vacuum 81, 2007, pp. 1114-1118.
(Continued)

*Primary Examiner* — Zulmariam Mendez
(74) *Attorney, Agent, or Firm* — Lerner, David, Littenberg, Krumholz & Mentlik, LLP

(57) ABSTRACT

A method for the antimicrobial provision of implant surfaces with silver, in which the method comprises an anodizing of the implant surface with an electrolyte, in which the electrolyte has a silver-yielding substance. Alternatively, the method comprises a silver implantation or a silver PVD deposition.

12 Claims, 4 Drawing Sheets

(51) Int. Cl.
  *A61L 27/06* (2006.01)
  *A61L 27/30* (2006.01)
  *A61L 27/54* (2006.01)

(56) References Cited

U.S. PATENT DOCUMENTS

| | | | |
|---|---|---|---|
| 2003/0060873 A1 | 3/2003 | Gertner et al. | |
| 2005/0221259 A1 | 10/2005 | Anderson | |
| 2007/0181221 A1 | 8/2007 | Pickford et al. | |
| 2007/0287027 A1* | 12/2007 | Justin et al. | 428/666 |
| 2008/0090414 A1* | 4/2008 | Chen et al. | 438/678 |
| 2008/0192493 A1* | 8/2008 | Villard | 362/373 |
| 2010/0206733 A1* | 8/2010 | Agg et al. | 205/50 |

FOREIGN PATENT DOCUMENTS

| | | |
|---|---|---|
| JP | 2005137801 A | 6/2005 |
| WO | 81/02667 A1 | 10/1981 |
| WO | 0143788 A2 | 6/2001 |
| WO | 2005103330 A1 | 11/2005 |
| WO | 2008002750 A2 | 1/2008 |

OTHER PUBLICATIONS

Zhao et al.: "Bactericidal and corrosive properties of silver implanted TiN thin films coated on AISI317 stainless steel" Surface and Coatings Technology, Elsevier, Amsterdam, NL, vol. 201, No. 9-11, Jan. 31, 2007, pp. 5676-5679.

Disegi J A ED—Bumgardner J D et al.: "Anodizing treatments for titanium implants" Biomedical Engineering Conference, 1997, Proceedings of the 1997 sixteenth Southern Biloxi, MS, USA Apr. 4-6, 1997, New York, NY, USA, pp. 129-132.

Jung-Yoon Cho, Kyung-Ho Kim, Kwang-Chul Choy, Keun-Taek Oh, Kyung-Nam Kim: "Photocatalytic antibacterial effect of TiO2 fihn formed on Ti and TiAg exposed to *Lactobacillus acidophilus*", Journal of Biomedical Materialy Research Part B: Applied Biomaterials, vol. 80B, No. 2, Jul. 18, 2006, pp. 353-359.

G.J.Chi et al.: "Antibacterial activity of anodized aluminum with deposited silver", Surface and Coatings Technology, vol. 157, No. 2-3, May 6, 2002, pp. 162-165.

Shirkhanzadeh M et al.: "Bioactive delivery systems for the slow release of antibiotics:Incorporation of AG<+> ions into microposous hydroxyapatite coatings", Materials Letters, North Holland Publishing Company, Amsterdam, NL, vol. 24, No. 1-3, Jun. 1, 1995, pp. 7-12.

* cited by examiner

ANTIMICROBIAL PROVISION OF TITANIUM AND TITANIUM ALLOYS WITH SILVER

CROSS REFERENCE TO RELATED APPLICATIONS

The present application is a national phase entry under 35 U.S.C. §371 of International Application No. PCT/EP2008/066604, filed Dec. 2, 2008, published in English, which claims the benefit of German Patent Application No. 10 2008 008 517.0, filed Feb. 11, 2008. The disclosures of said applications are incorporated by reference herein.

SUBJECT OF THE PRESENT INVENTION

The present invention relates to a method for the antimicrobial provision of titanium and titanium alloys with silver, in particular a method which permits an antimicrobial provision of titanium and titanium alloys with silver which makes possible a controlled release of silver ions over a particular period of time.

BACKGROUND OF THE INVENTION

Numerous methods are known for the surface treatment of titanium, for instance Type I-V anodizing, electropolishing, plasma nitriding etc. Likewise, numerous methods are known for the antimicrobial provision of surfaces with silver, for instance deposition from the vapour phase (PVD), from oversaturated solution, or by ion implantation.

In addition, a coating of silver on titanium is known from "Antimicrobial titanium/silver PVD coatings on titanium" by Andrea Ewald et al., published on 24 Mar. 2006 in BioMedical Engineering OnLine 2006, 5:22 doi:10.1186/1475-925X-5-22.

SUMMARY OF THE INVENTION

The object of the invention is to provide the method which permits an improved antimicrobial provision of titanium and titanium alloys with silver, which makes possible a controlled release of silver ions over a particular period of time.

The object of the invention is solved by the subject matter of the independent claims, with advantageous developments thereof being embodied in the dependent claims.

According to an example embodiment of the invention, a method is made available for the antimicrobial provision of implant surfaces with silver, the method comprising an anodizing of the implant surface in the presence of an electrolyte, the electrolyte comprising a silver-yielding substance.

Thereby, a simultaneous establishing of a silver deposit and a surface treatment, for instance for hardening and for increasing the wear resistance, is provided.

According to an example embodiment of the invention, the silver-yielding substance comprises a silver salt.

Thereby, a high number of silver ions can be easily provided in an electrolyte.

According to an example embodiment of the invention, the silver salt comprises silver nitrate.

Silver nitrate is soluble relatively easily in water, so that an aqueous solution can be used as electrolyte.

According to an example embodiment of the invention, the silver is at least partially reduced from silver ions by a reducing agent.

A reducing agent is able to make available for the silver ions the electrons which are missing for a required reduction. The reducing agent can also be an electron source acting from the exterior.

According to an example embodiment of the invention, the electrolyte comprises the reducing agent.

In this way, the reducing agent can be provided directly in the electrolyte.

According to an example embodiment of the invention, the reducing agent comprises sodium borohydride.

Sodium borohydride is a particularly suitable reducing agent, in particular for silver ions in an aqueous solution.

According to an example embodiment of the invention, the anodizing comprises an anodizing of Type II.

In this way, a hardening and an introduction of silver into relatively great depths of for example 5 to 10 micrometers can be achieved.

According to an example embodiment of the invention, the anodizing comprises an anodizing of Type III.

In this way, a depositing of a defined layer can take place on the implant surface, without substantially affecting the base substance of the implant.

According to an example embodiment of the invention a solution is added to the electrolyte during anodizing which has a concentration of $1 \times 10 \exp{-4}$ M to $1 \times 10 \exp{-2}$ M, preferably approximately $1 \times 10 \exp{-3}$ M silver nitrate and a concentration of $2 \times 10 \exp{-4}$ M to $2 \times 10 \exp{-2}$ M, preferably approximately $2 \times 10 \exp{-3}$ M sodium borohydride.

These concentrations have proved to be particularly advantageous for the application process.

According to an example embodiment of the invention, the silver ions are reduced and are incorporated into the anodizing layer of the implant surface or an oxide layer situated thereon before a precipitation as nanoparticles.

In this way, the silver components can become integral components of the base material or of the coating.

According to an example embodiment of the invention, a method for the antimicrobial provision of implant surfaces with silver comprises a silver implantation.

By a silver implantation, silver can be introduced for example by a sputtering process into the uppermost layers of an implant surface.

According to an example embodiment of the invention, the method further comprises an anodizing of the implant surface.

In this way, the implant surface can be surface-treated after a silver implantation, for instance hardened or made more wear-resistant against wear of soft or hard tissue.

According to an example embodiment of the invention, parameters of a silver implantation are selected so that a penetration depth of the silver lies between 0.5 and 2 micrometers, in particular 1 micrometer.

In this way, a defined delivery of silver can be achieved over a particular period of time.

According to an example embodiment of the invention, a method for the antimicrobial provision of implant surfaces with silver comprises a physical gas phase deposition.

In this way, a defined coating can be applied onto the surface of an implant.

According to an example embodiment of the invention, the method further comprises an anodizing of the implant surface.

In this way, the implant surface can be surface-treated after a silver implantation, for instance hardened or made more wear-resistant against wear of soft or hard tissue.

According to an example embodiment of the invention, the physical gas phase deposition is carried out alternately with silver and with titanium.

In this way, not only a silver implantation, but a silver-titanium covering layer can be applied onto the base material, and namely by the alternating in defined layer thicknesses or a matrix for the chronologically controlled delivery of silver.

According to an example embodiment of the invention, the physical gas phase deposition is carried out simultaneously with silver and with titanium.

In this way, not only a silver implantation but also a silver-titanium covering layer can be applied onto the base material, in which through the simultaneous application a faster coating can be achieved by simultaneous coating.

According to an example embodiment of the invention, the covering layer applied by physical gas phase deposition has a thickness between 1 and 3 micrometers, in particular 1 micrometer.

In this way, a particularly resistant coating can be applied.

According to an example embodiment of the invention, the anodizing comprises an anodizing of Type II or of Type III.

In this way, a hardening and an introduction of silver can be achieved into relatively great depths of for example 5 to 10 micrometers (Type II), or a deposition of a defined layer on the implant surface can take place, without substantially affecting the base substance of the implant (Type III).

According to an example embodiment of the invention, a computer program is provided which, when it is executed through a processor, is designed to carry out the method according to the invention.

According to an example embodiment of the invention, a computer-readable medium is provided, on which the computer program according to the invention is stored.

Through an anodizing, in particular of Type II and III, and the combined silver deposition it is made possible that silver or silver atoms are incorporated into the anodizing layer and thus become a component of the base material. The aim here is to fundamentally increase the Ag layer adhesion and to make possible a controlled release of the silver ions over a period of at least 10 days. In addition, the advantages of the anodizing can be combined with those of the silver doping/alloying such that the release of silver ions in the living tissue takes place in a controlled manner and a concentration is reached which is sufficiently high to achieve an antimicrobial effect for, for example, at least 10 days, which is in addition low enough not to act cytotoxically on the surrounding tissue. Typical values for the release of silver ions after 24 h in buffered Ringer's solution lie between 0.5 ppb and 50 ppb, depending on the pre-treatment of the surface.

The individual features can of course also be combined with each other, whereby in part also advantageous effects can occur which go beyond the sum of the individual effects.

These and other aspects of the present invention are explained and clarified by reference to the example embodiments described hereafter.

BRIEF DESCRIPTION OF THE DRAWINGS

Example embodiments are described below with reference to the following drawings.

DETAILED DESCRIPTION OF EXAMPLE EMBODIMENTS

The antimicrobial effect of silver ions or—salts can be achieved for example by stable silver nanoparticles. Thereby, an antimicrobial activity of silver nanoparticles can be achieved, which inhibits growth in the case of various bacteria. Silver nanoparticles of various concentrations can be used for this. As a result, various bacteria can already be suppressed at low concentrations of silver nanoparticles. The effect of a generation of free radicals is responsible for this in the case of silver nanoparticles for an inhibiting of microbial growth. Silver nanoparticles can be used as effective growth inhibitors for various microorganisms, whereby they can be used for various medical apparatus and antimicrobial control systems.

An anodizing of Type II and III are methods of anodizing titanium which are relevant for medical technology. The aim here is to stabilize the natural oxide layers (e.g. rutile), which are unsuitable per se, so that a minimal Ti wear occurs in contact with soft or hard tissue. Through Type II, in addition, the fatigue strength is increased by approximately 15-30%.

Figure 2:
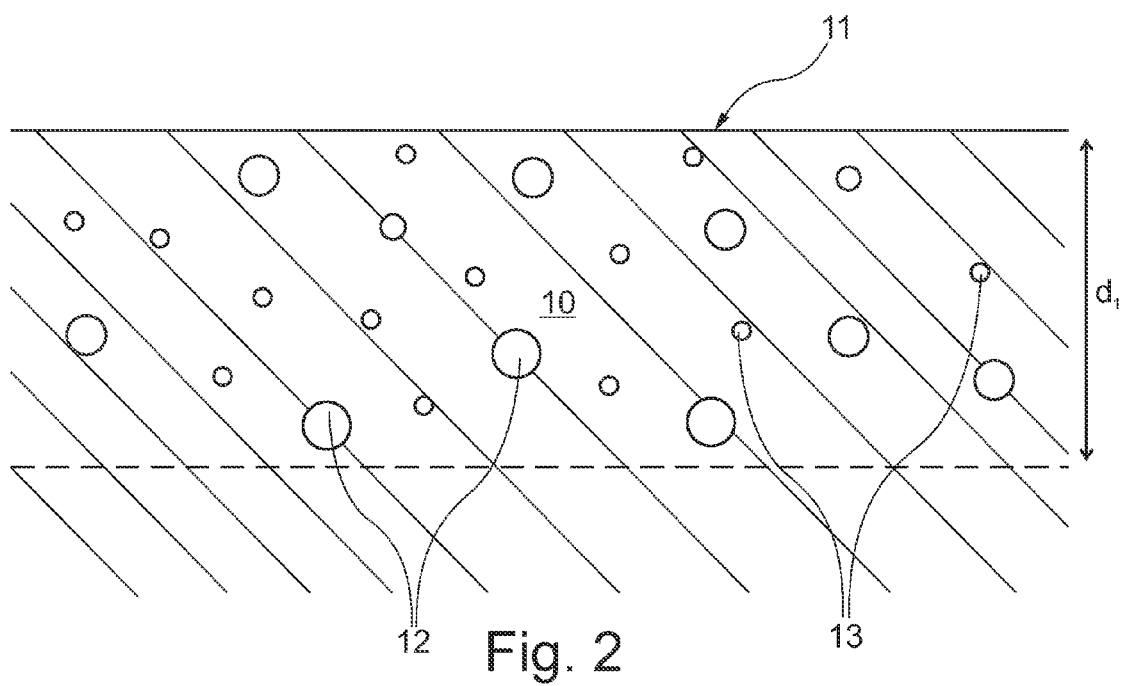
FIG. 2 shows a layer structure according to a Type III anodizing.

In Type II anodizing, a basic electrolyte is used. The first step of a Type II anodizing is an electrolytic treatment in a basic bath. A voltage is applied between the material and the bath. This causes the surface material to be melted point by point over the entire surface 11. This procedure removes the original oxide layer and brings about an oxygen- and silicon diffusion 12 up to a depth d1 into the material 10. This depth can be for example 5 to 10 micrometers. The material 10 can be titanium or a titanium alloy. Likewise, an oxidizing of the titanium can take place as $TiO_x$ 13. In addition, a new porous oxide layer is grown on the surface 11. In a second step, this porous oxide layer is removed by blasting with glass spherules. The resulting surface structure is shown in FIG. 2.

The diffused oxygen forms partially oxides 13, which have a very great hardness. Oxygen 12 and oxides 13 are embedded into the material interstitially or forming intermediate spaces, forming an integral part of the material 10. The region of a diffusion is named conversion layer d1.

In Type III an acid electrolyte is used. In a first step, the original oxide layer is removed in an acid bath. The electrolytic process follows in a second step. A voltage is again applied in an acid bath between the material and the bath. The voltage is used to control the thickness d2 of a new titanium dioxide 13 $TiO_2$ oxide layer on the surface 11. This thickness d2 can be for example 0.02 to 0.2 micrometers. The parts are hereafter not blasted with glass spherules, because this would destroy the oxide layer of a defined thickness d2. The resulting surface structure is shown in FIG. 2.

The surface 14 of anodized Type III shows a similar structure to a non-anodized surface. The main difference is the thickness of the oxide layer d2, which is smaller than the thickness d1 by more than one order of magnitude. The transparency and defined thickness d2 of a layer makes possible a colouring of the surface. The colour is produced by a light interference which originates from incident external light 21, 23, which is partially reflected 22 by the surface layer 14, and is partially reflected 24 by the material surface 11. The colour depends here on the layer thickness which can be controlled by the anodizing process.

In the separating of silver from the oversaturated solution, an aqueous solution of for example $1\times10exp-3$ M silver nitrate is mixed in the proportion approximately 1:3 with an aqueous solution of 2×10exp−3 M sodium borohydride as reducing agent. On the mixing of the two solutions, the Ag ions are reduced and precipitated as nanoparticles in the solution and are stabilized by stirring. The 3.3 nM solution can then be diluted to the desired concentration.

According to an embodiment of the invention, a solution of a silver salt and of a reducing agent is added to the electrolyte during anodizing. On mixing of the solution with the electrolyte, the Ag ions can now be reduced and still incorporated into the sample surface or the oxide layer before precipitating as nanoparticles. The reducing can take place by any desired suitable means.

Figure 1:
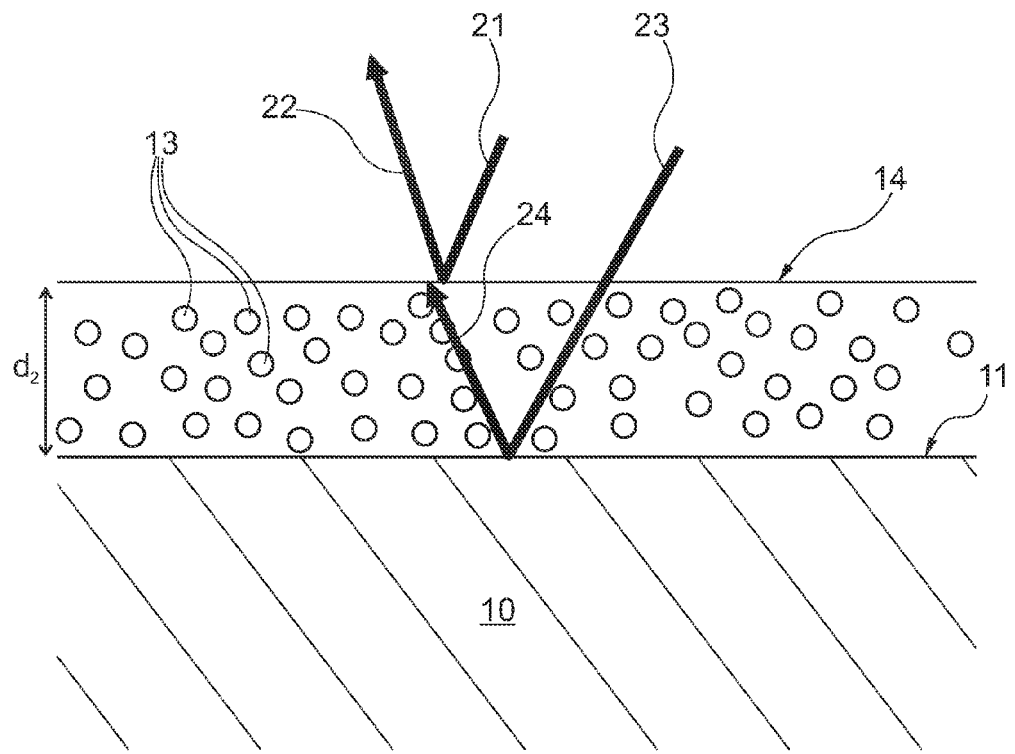
FIG. 1 shows a layer structure according to a Type II anodizing.
Figure 3:
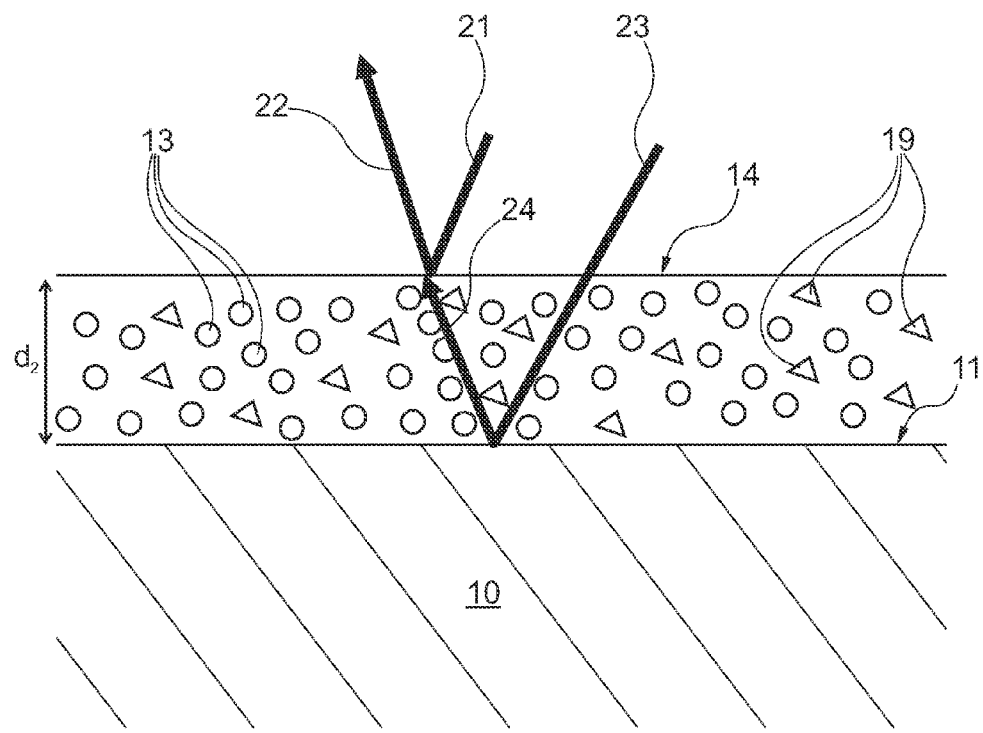
FIG. 3 shows a layer structure with embedded silver according to a Type II anodizing.
Figure 4:
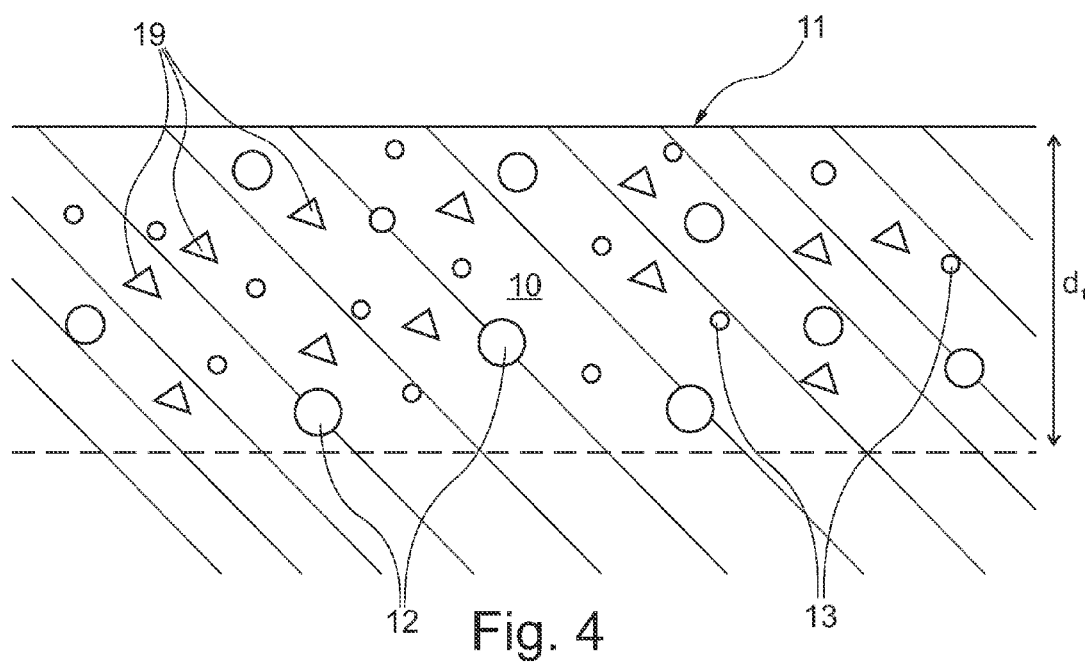
FIG. 4 shows a layer structure with embedded silver according to a Type III anodizing.

The result can be seen in FIG. 3 and FIG. 4. These two illustrations correspond substantially to FIG. 1 and FIG. 2, but with the difference that in the structure shown in FIG. 3 and FIG. 4 an embedding of silver 19 has taken place. Through the presence of reduced silver in the electrolyte, silver 19 penetrates up to a depth of approximately d1 on the anodizing of Type II (FIG. 4). In addition, silver 19 precipitates together with the titanium dioxide 13 and leads to a layer thickness of d2 (FIG. 3) on the otherwise substantially unchanged base material 10.

In particular, according to an embodiment of the invention, on anodizing of Type II/III, a solution of 1×10exp−3 M silver nitrate and of 2×10exp−3 M sodium borohydride can be added to the electrolyte. On mixing the two solutions with the electrolyte, the Ag ions can now again be reduced here and still incorporated into the sample surface 11 (FIG. 2, FIG. 4) or the oxide layer (FIG. 1, FIG. 3) before the precipitation as nanoparticles 19. The reducing takes place here by the reducing agent sodium borohydride, likewise dissolved in the electrolyte.

It is noted that instead of silver nitrate, other suitable silver salts can also be used. The required silver ions can also be produced intrinsically. In addition, the use is not restricted to the use of sodium borohydride. Instead of this, other suitable reducing agents can also be used. Alternatively, suitable agents, acting as catalyst, can also be used in order to achieve a precipitation or deposition of silver.

Alternatively, a provision of a titanium or titanium alloy surface with silver can also take place by means of an Ag ion implantation or a PVD coating.

An Ag ion implantation is carried out in a vacuum chamber at low pressures of 10exp−4 mbar. The metal ions are accelerated after production onto the titanium surface and penetrate into the latter up to a depth of one to two micrometers.

This process is now carried out alternately with Ag and with Ti atoms, in order to apply not only an Ag implantation but an Ag—Ti covering layer onto the base material.

The term physical gas phase deposition (Physical Vapour Deposition, abbreviated to PVD) designates a group of vacuum-based coating methods or thin layer technologies, in which the layer is formed directly by condensation of a material vapour of the starting material. The material which is to be deposited is generally present in solid form in the generally evacuated coating chamber. The material, which is designated as the target, is vaporized by bombardment with laser beams, magnetically deflected ions or electrons and by arc discharge. The extent of the proportion of atoms, ions or larger clusters in the vapour is different from method to method. The vaporized material moves either ballistically or guided through electric fields through the chamber and in so doing impinges onto the parts which are to be coated, where the layer formation occurs. So that the vapour particles also reach the components and are not lost by scattering on the gas particles, operations must be carried out in vacuum. Typical operating pressures lie in the range of 10-4 Pa to approximately 10 Pa. As the vapour particles spread in a straight line, areas which are not visible from the site of the vapour source are coated at a lower coating rate. If all areas are to be coated as homogeneously as possible, the parts must be moved in a suitable manner during coating. This takes place generally by rotation of the substrate. When the vapour particles now impinge onto the substrate, they begin to deposit themselves on the surface by condensation. The particles do not remain here at the original location at which they impinge onto the substrate, but rather move, depending on how high their energy is, along the surface (surface diffusion), in order to find an energetically more favourable place. These are sites on the crystal surface with as many neighbours as possible (higher binding energy).

A process of a PVD coating can be carried out in commercially available PVD systems. Here, a PVD covering layer of for example approximately 2 micrometers consisting of Ti and Ag atoms is applied simultaneously onto the Ti base material. For this PVD coating on titanium, for example the coating can be carried out for example with a thickness for example of approximately two micrometers on the titanium surface by simultaneous vaporization of two materials, for example titanium and silver, in an inert argon atmosphere. Here, two precursors can then be used at the same time. Silver contents of 0-100% can be realized here in the covering layer.

An ion implantation is a possibility for the modifying of surface characteristics of materials. It is similar to a coating process, but it does not cause any build-up of a layer onto the surface. Originally developed for use in semiconductor applications, an ion implantation uses a high energy ion beam of e.g. positively charged atoms for modifying a surface structure and a surface chemistry of materials at low temperatures. Here, however, the process does not bring about any disadvantageous effects in the component dimensioning or in material characteristics. Several surface characteristics can be improved by an ion implantation, including the hardness or resistance to wear or chemical stress or of the friction coefficient. The process can be applied to almost any material, including most metals, likewise on ceramics and polymers. However, the effects of the process are typically material-specific. In particular, components treated with ion implantation can be prostheses or implants of titanium, which can be made harder and more able to support loads by the process of ion implantation. The process of an ion implantation is carried out in a vacuum chamber at very low pressures, with a large number of ions bombarding the surface and penetrating into the surface, then interacting with the atoms of the substrate directly under the surface. A typical depth of an ion penetration is a fraction of a micrometer. The interactions of the energetic ions with the material modify the surface and endow it with significantly different characteristics from the original material. Specific changes in characteristic depend on the choice of the treatment parameters of the ion bombardment, for example the ion species, the energy and the total number of ions applied onto the surface. An ion implantation offers numerous advantages for the treating of surfaces, a great advantage being in the possibility of a selective modification of the surface without having a disadvantageous effect on the material characteristics, because the process is carried out at low substrate temperatures. The process is, in addition, easily controllable and reproducible and can be tailored to the modification of different surfaces in a desired manner.

The advantages of anodizing can be combined with those of silver doping/alloying for the method according to the invention such that the release of Ag ions in the living tissue takes place in a controlled manner and a concentration can be reached which is sufficiently high to achieve an antimicrobial effect for example at least 10 days, but on the other hand can be low enough not to act in a cytotoxic manner on the surrounding tissue. Typical values for the release of Ag ions after 24 h in buffered Ringer's solution lie between 0.5 ppb and 50 ppb, depending on the pre-treatment of the surface. Ti—Ag systems produced through an Ag ion implantation or through a PVD coating can be subsequently treated by an anodizing of Type II or Type III in a suitable manner. This can take place optionally.

Figure 5:
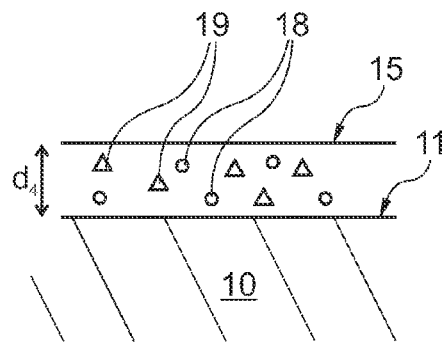
FIG. 5 to FIG. 10 show surface structures which are able to be produced by methods according to example embodiments of the invention.
Figure 6:
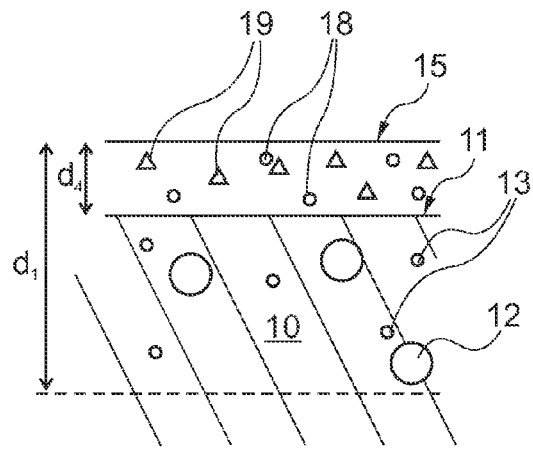
Figure 7:
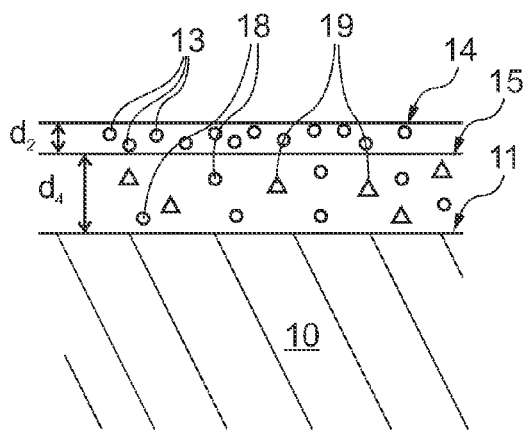

FIG. 5 shows a material 10 coated by a PVD process with a layer thickness d4, a coating of Ti 18 and Ag 19 having been applied here. The layer thickness can be in the order of approximately a few micrometers, for instance two micrometers. However, a coating only of Ag 19 can also be applied. FIG. 6 shows the material 10 shown in FIG. 5, after a subsequent anodizing of Type II, analogous to FIG. 2. FIG. 7 shows the material 10 shown in FIG. 5 after an anodizing of Type III, analogous to FIG. 1. The thicknesses of the layers or depths d1 and d2 are analogous to FIG. 2 and FIG. 1.

Figure 8:
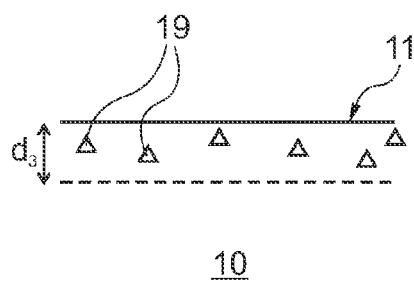
Figure 9:
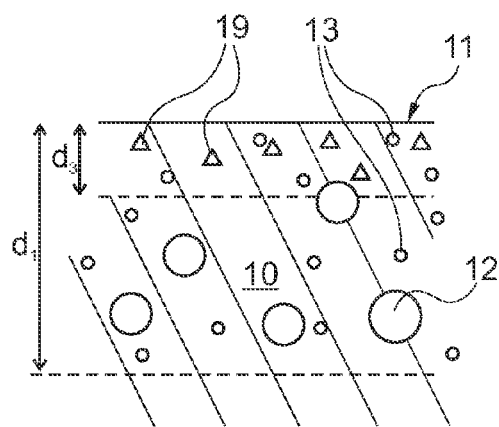
Figure 10:
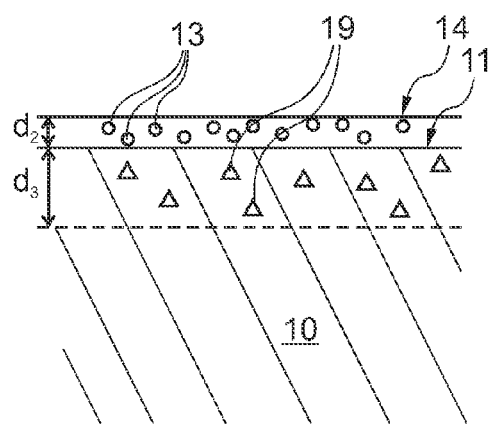

FIG. 8 shows a material 10 treated with an Ag implanting up to a penetration depth of d3. The penetration depth can be in the order of approximately a few micrometers, for instance one micrometer. However, a coating only of Ag 19 can also be applied. FIG. 9 shows the material 10 shown in FIG. 8, after a subsequent anodizing of Type II, analogous to FIG. 2. FIG. 10 shows the material 10 shown in FIG. 8 after an anodizing of Type III, analogous to FIG. 1. The thicknesses of the layers or depths d1 and d2 are analogous to FIG. 2 and FIG. 1.

Figure 11:
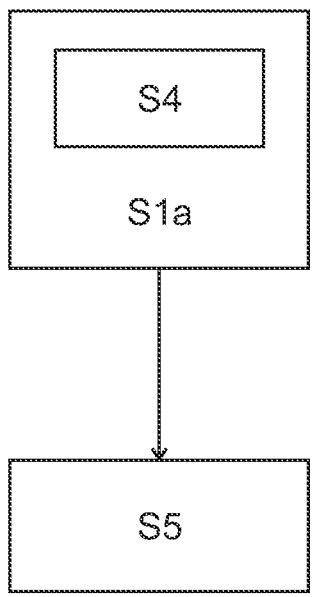
FIG. 11 to FIG. 13 show diagrammatic sequences of methods according to example embodiments of the invention.

FIG. 11 shows the diagrammatic sequence of a method according to an embodiment of the invention. In step S1a an anodizing of Type II is carried out, as described above. Here, in step S4 a mixing of the electrolyte with a silver salt or equivalent is carried out, in order to perform a process which leads in step S5, as described above, to a build-up of the surface structure according to FIG. 4.

Figure 12:
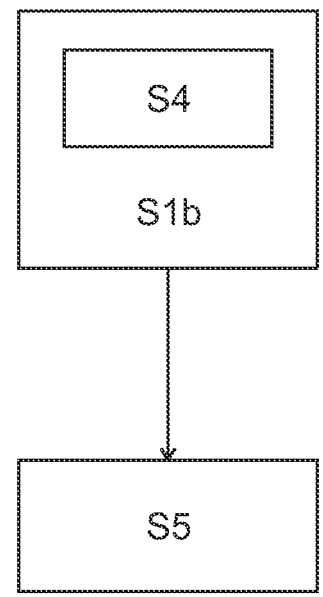

FIG. 12 shows the diagrammatic sequence of a method according to an embodiment of the invention. In step S1b an anodizing of Type III is carried out, as described above. Here, in step S4 a mixing of the electrolyte with a silver salt or equivalent is carried out, in order to perform a process which leads in step S5, as described above, to a build-up of the surface structure according to FIG. 3.

Figure 13:
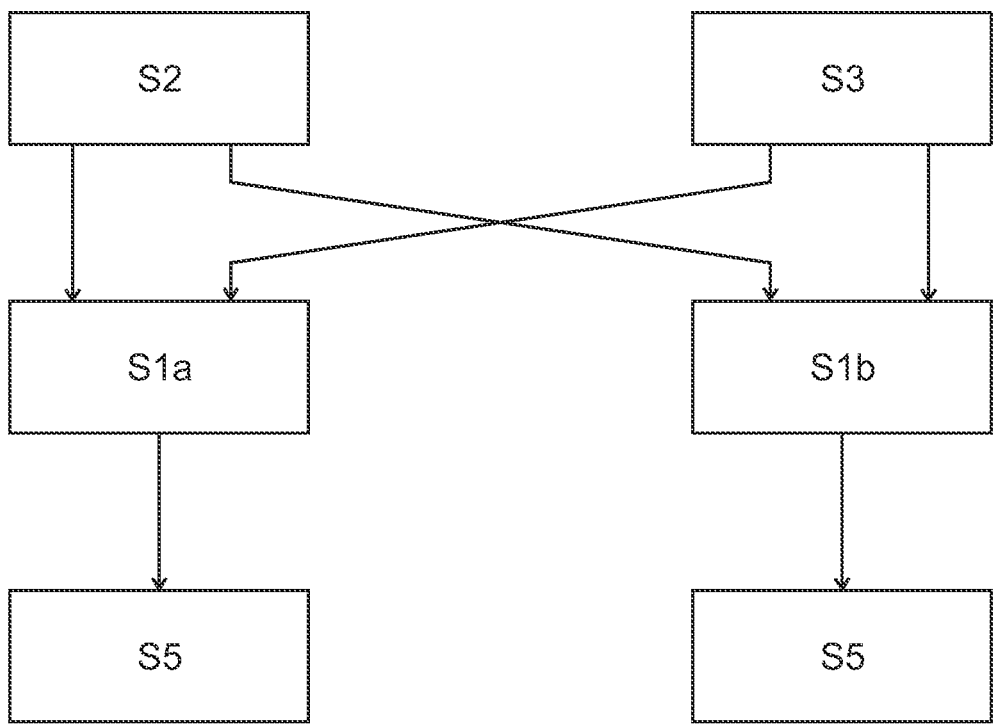

FIG. 13 shows a collection of possible diagrammatic sequences of a method according to an embodiment of the invention. In step S2 an Ag implantation is carried out, as described above. In step S3 a PVD process is carried out, as described above. Following step S2 or step S3, in step S1a an anodizing of Type II is carried out, as described above, or in step S1b an anodizing of Type III is carried out, as described above, which respectively leads in step S5 to a coating. In the sequence of steps S2, S1a, S5, this leads, as described above, to a build-up of the surface structure according to FIG. 9. In the sequence of steps S2, S1b, S5, this leads, as described above, to a build-up of the surface structure according to FIG. 10. In the sequence of steps S3, S1a, S5, this leads, as described above, to a build-up of the surface structure according to FIG. 6. In the sequence of steps S3, S1b, S5, this leads, as described above, to a build-up of the surface structure according to FIG. 7.

It is noted that the term "comprise" does not rule out further elements or method steps, likewise the term "a" does not rule out several elements and steps.

The reference numbers which are used serve merely to increase the comprehensibility and are in no way regarded as restrictive, with the scope of protection of the invention being expressed by the Claims.

The invention claimed is:

1. A method for the antimicrobial provision of implant surfaces with silver, wherein the implant is made of titanium or titanium alloy, the method comprising the step of:
    implanting silver ions into a titanium or titanium alloy surface with a penetration depth between 0.5 and 2 micrometers by accelerating the silver ions onto the titanium or titanium alloy surface and thereafter precipitating silver onto a titanium or titanium alloy implant surface in a coating having a thickness of 0.02 to 0.2 micrometers by anodizing the implant surface in the presence of an electrolyte comprising:
    a silver-yielding substance and a reducing agent, wherein the silver is reduced at least partially from silver ions by the reducing agent so that the implant is configured to deliver silver ions in a defined manner over a particular period of time.

2. The method according to claim 1, in which the silver-yielding substance comprises a silver salt.

3. The method according to claim 2, in which the silver salt comprises silver nitrate.

4. The method according to claim 1, in which the reducing agent comprises sodium borohydride.

5. The method according to claim 1 further comprising upon anodizing, adding a solution to the electrolyte which has a concentration of $1 \times 10^{-4}$ M to $1 \times 10^{-2}$ M, silver nitrate and a concentration of $2 \times 10^{-4}$ M to $2 \times 10^{-2}$ M, sodium borohydride.

6. The method according to claim 1, in which silver ions are reduced and are incorporated before precipitation as nanoparticles into the anodizing layer of the implant surface or an oxide layer.

7. A method for the antimicrobial provision of implant surfaces with silver, wherein the implant is made of titanium or titanium alloy, the method comprising the steps of:
    implanting silver ions in a titanium or titanium alloy implant surface by accelerating silver ions onto the surface of the titanium or titanium alloy and thereafter
    anodizing the implant surface in a silver containing substance and electrolyte solution so as to provide a first layer with a first thickness and a second layer with a second thickness, both layers including silver ions so that the implant is configured to release silver ions in a controlled manner over a period of at least 10 days.

8. The method according to claim 7, in which parameters of a silver implantation are selected so that a penetration depth of the silver ions lies between 0.5 and 2 micrometers.

9. A method for the antimicrobial provision of implant surfaces with silver, wherein the implant is made of titanium or titanium alloy, the method comprising the step of:
    producing and accelerating silver ions into a surface of the titanium or titanium alloy implant in a vacuum chamber so as to implant silver ions at a depth lying between 0.5 and 2 microns below the surface;
    thereafter anodizing the implant surface in the presence of an electrolyte comprising a silver-yielding substance and a reducing agent, wherein the silver is reduced at least partially from silver ions by the reducing agent so as to diffuse silver ions up to a depth between 5 and 10 micrometers so that the implant is configured to release silver ions in a controlled manner over a period of at least 10 days.

10. The method according to claim 9, in which the reducing agent comprises sodium borohydride.

11. The method according to claim 9 further comprising upon anodizing, adding a solution to the electrolyte which has a concentration of $1\times10^{-4}$ M to $1\times10^{-2}$ M, silver nitrate and a concentration of $2\times10^{-4}$ M to $2\times10^{-2}$ M, sodium borohydride.

12. The method according to claim 7 further comprising upon anodizing, adding a solution to the electrolyte which has a concentration of $1\times10^{-4}$ M to $1\times10^{-2}$ M, silver nitrate and a concentration of $2\times10^{-4}$ M to $2\times10^{-2}$ M, sodium borohydride.

* * * * *